(12) United States Patent
Schöb

(10) Patent No.: US 6,386,505 B2
(45) Date of Patent: May 14, 2002

(54) CLAMPING APPARATUS

(75) Inventor: Reto Schöb, Volketswil (CH)

(73) Assignee: Levitronix LLC, Waltham, MA (US)

( * ) Notice: Subject to any disclaimer, the term of this patent is extended or adjusted under 35 U.S.C. 154(b) by 0 days.

(21) Appl. No.: 09/801,069

(22) Filed: Mar. 6, 2001

(30) Foreign Application Priority Data

Mar. 6, 2000 (EP) ............................................. 00810184

(51) Int. Cl.⁷ ................................................ F16K 7/04
(52) U.S. Cl. ........................ 251/7; 251/65; 251/129.07
(58) Field of Search ...................... 251/7, 4, 65, 129.07, 251/129.15

(56) References Cited

U.S. PATENT DOCUMENTS

| | | | |
|---|---|---|---|
| 2,835,252 A | | 5/1958 | Mauchel |
| 3,278,153 A | * | 10/1966 | Dallas ............................ 251/7 |
| 4,014,318 A | * | 3/1977 | Dockum et al. ............. 137/527 |
| 4,191,359 A | | 3/1980 | Andersson |
| 4,524,802 A | * | 6/1985 | Lawrence et al. .............. 251/7 |
| 4,969,424 A | * | 11/1990 | Klomp .................... 251/129.1 |
| 5,482,446 A | | 1/1996 | Williamson |
| 5,529,281 A | | 6/1996 | Brudnicki |
| 5,868,108 A | * | 2/1999 | Schmitz et al. ......... 251/129.16 |
| 6,198,370 B1 | * | 3/2001 | Schmitz .................... 251/129.1 |

FOREIGN PATENT DOCUMENTS

| | | |
|---|---|---|
| EP | 0718001 A2 | 6/1996 |
| FR | 2321904 | 3/1977 |

* cited by examiner

Primary Examiner—Henry C. Yuen
Assistant Examiner—John Bastianelli
(74) Attorney, Agent, or Firm—Townsend and Townsend and Crew LLP

(57) ABSTRACT

A clamping apparatus for clamping off a hose in a fluid system for biological liquids, in particular blood, which has a movably arranged closing member having a closing piece for clamping off the hose, having permanent magnetic holding device which is arranged and designed in such a manner that it can hold the closing member against a force in two different stable equilibrium positions, namely an open position and a closed position, without it being necessary to supply energy to the permanent magnetic holding device for the holding in the respective equilibrium position, and having actuation means in order to move the closed member out of the open position into the closing position.

11 Claims, 6 Drawing Sheets

CLAMPING APPARATUS

Figure 1:
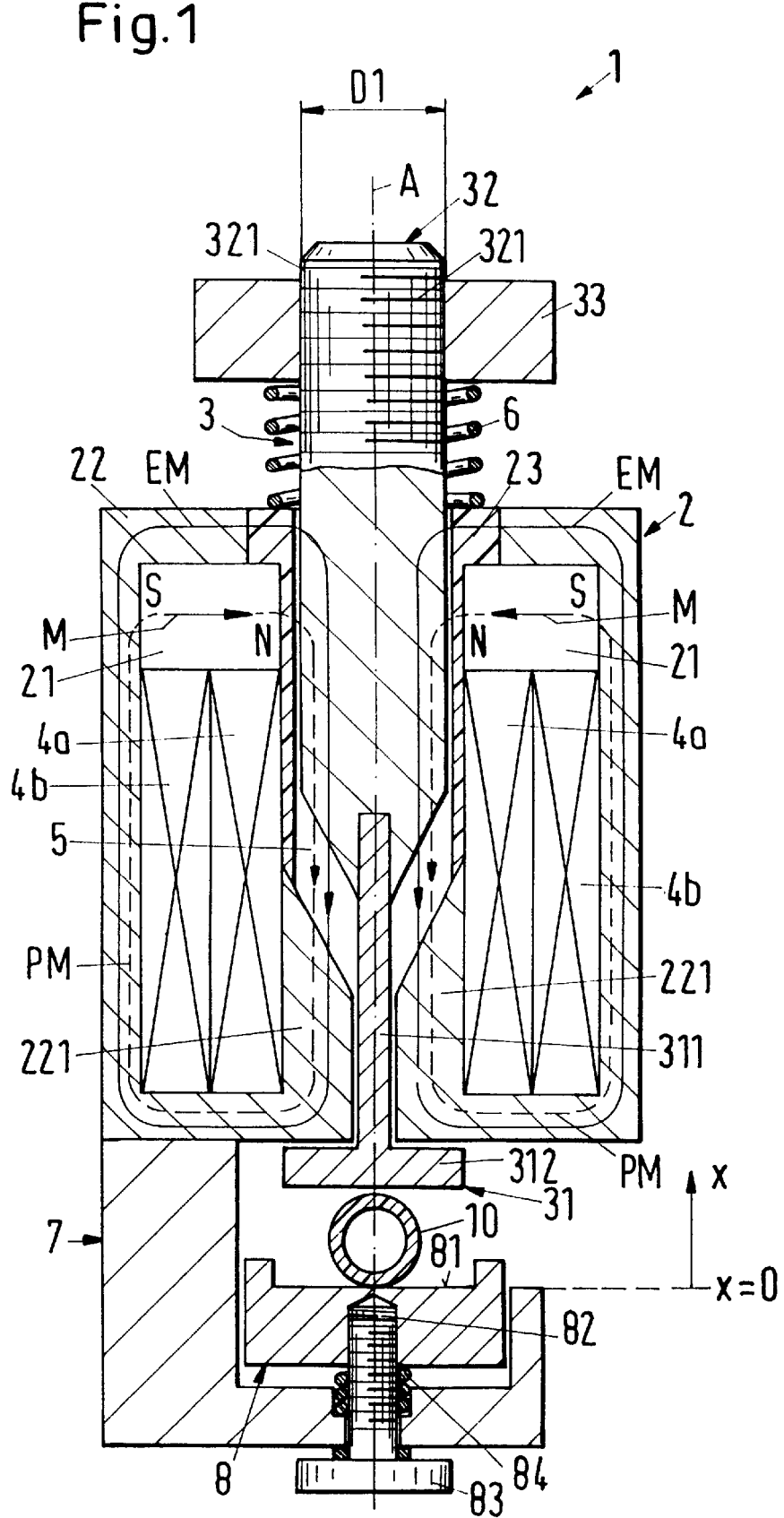

The invention relates to a clamping apparatus for clamping off a hose in a fluid system for biological liquids, in particular blood.

Fluid systems for biological liquids typically comprise a pump apparatus for the fluid to be forwarded which is connected via hoses to a circulation or to other elements of the fluid system respectively. As an example for a fluid system of this kind, heart-lung machines may be named here, which are e.g. connected during a heart operation to the blood circulation of the patient in order to take over the functions of the heart and to maintain the blood circulation. In this it is very important that no air bubbles wherever possible are present in the blood which is forwarded into the circulation of the patient, since these represent a serious endangering of the patient. Therefore a bubble detector and a clamping apparatus are usually provided downstream from the pump in heart-lung machines. As soon as the bubble detector detects an air bubble, the clamping apparatus must clamp off the hose through which the forwarded blood flows into the body of the patient and thereby interrupt the blood supply to the patient as rapidly as possible in order that the air bubble can not penetrate into the body circulation of the patient. The clamping apparatus thus serves as an on/off switch for the flow connection between the blood pump and the body circulation of the patient. In order that the clamping apparatus can interrupt the flow connection sufficiently rapidly through clamping off the hose, it is desirable that its switching time amounts to less than 100 milliseconds, preferably at most 80 milliseconds.

Clamping apparatuses are known in which the clamping off takes place by means of a spindle and a step motor which drives the spindle. These apparatuses however have the disadvantage that they are constructionally complicated and expensive and that relatively large and powerful step motors are required for a sufficient speed. In addition, clamping apparatuses of this kind are self locking due to the spindle drive. In the event that the electrical system fails, it is therefore very difficult, if at all possible, to open or close the clamping apparatus manually.

Furthermore, clamping apparatuses are known in which the closing member which clamps off the blood conducting hose is electromagnetically actuated. The closing member is moved by means of an electromagnet, mainly against the force of a spring, into the closure position and is held there, or, on the contrary, is held in the open position against the force of a spring by an electromagnet. Through deactivation of the electromagnet the closing member then moves into the open position or into the closure position dependent of the specific design as a result of the spring force. Disadvantageous in clamping apparatuses of this kind is their high energy consumption, since energy is constantly required for at least one holding state, namely the holding of the closing member in the open position or the holding in the closure position, in order to supply the electromagnet with current. The constant current flow furthermore leads to a disadvantageous heat production. The high energy requirement is a considerable disadvantage in particular in portable or mobile systems respectively, since systems of this kind are usually supplied by batteries. Also in regard to situations in which the heart-lung machine can be operated only with emergency power it is desirable to keep the current requirement as low as possible. In addition, such electromagnetically operated clamping apparatuses also have the disadvantage that they can not be opened or closed manually when the electrical system fails.

Starting from this prior art, an object of the invention is therefore to propose a clamping apparatus for clamping off a hose in a fluid system for biological liquids which does not have these disadvantages. In particular the clamping apparatus should require as little energy (current) as possible during operation and be constructionally simple and as compact as possible. It should enable sufficiently rapid switching times of less than about 100 milliseconds and in addition be manually actuatable in a simple manner.

Thus in accordance with the invention a clamping apparatus for clamping off a hose in a fluid system for biological fluids, in particular blood, is proposed comprising a movably arranged closing member having a closing piece for clamping off the hose, comprising a permanent magnetic holding device which is arranged and designed in such a manner that it can hold the closing member against a force in two different stable equilibrium positions, namely an open position and a closing position, without it being necessary to supply energy to the permanent magnetic holding device for the holding in the respective equilibrium position, and comprising actuation means in order to move the closing member out of the open position into the closing position.

The permanent magnetic holding device is thus designed in such a manner that two stable equilibrium positions exist for the closing member, namely on the one hand an open position in which a hose which is laid in into the clamping apparatus is not or only slightly clamped so that the liquid can flow through the hose, and on the other hand a closure position in which the hose is clamped off through the closure position of the closing member so that no liquid can flow through the hose any longer. No energy in the form of current is required for holding the closing member in the two equilibrium positions. The closing member is held in the two equilibrium positions purely passively, namely permanent magnetically, which is a quite considerable advantage in regard to the energy consumption.

In addition no spindle drives or other self locking drives are required for the actuation of the clamping apparatus, for which reason the clamping apparatus is constructionally simple, very compact and in particular also manually actuatable, which means that it can be brought manually into the open position and into the closure position.

The actuation means preferably comprise at least one coil which is arranged in such a manner that it can exert an electromagnetic force on the closing member in the direction towards the closure position or in the direction towards the open position. Through activation of the coil, in addition to the permanent magnetic holding force, an electromagnetic force is produced which deflects the closing member out of its one stable equilibrium position to such an extent that it assumes its other equilibrium position. The coil need thus be actuated only if the closing member is to be brought from the open position into the closure position or conversely from the closure position into the open position.

In a preferred exemplary embodiment the closing member comprises two limbs and a transverse bar, with the limbs being connected to the transverse bar at a spacing from one another. The permanent magnetic holding device then comprises two permanent magnetic holders, each of which surrounds a limb in each case, and in which the closure piece is arranged at the transverse bar between the two limbs. Furthermore, for each limb of the closing member at least one coil which surrounds the limb for exerting an electromagnetic force on the limb is preferably provided. This exemplary embodiment is distinguished by its particularly reliable operating behavior.

Two separate coils are preferably provided as actuation means for the closing member or for each limb of the closing member, with a separate control and supply apparatus being provided in each case for each of the two separate coils. Through this measure an advantageous fault tolerance can be realized, which increases the operating reliability. If namely one of the two separate coils or one of the two control and supply apparatuses drops out as a result of a fault, for example through a break in a line or in a cable respectively or another defect, then the closing member can continue to be operated electromagnetically with the coil which is still fault free, so that the clamping apparatus remains completely capable of functioning.

A further advantageous measure consists in providing at least one spring element which acts on the closing member and which is arranged in such a manner that the spring force acts opposite to the magnetic force which the permanent magnetic holding device exerts on the closing member. Through this measure the clamping apparatus can be matched in a simple way to the properties of the respective hose which is used.

The clamping apparatus in accordance with the invention is in particular suitable for combining with a pump apparatus for forwarding a biological fluid, especially for combining with a blood pump, for example in a heart-lung machine.

Further advantageous measures and preferred embodiments of the invention result from the independent claims.

Figure 2:
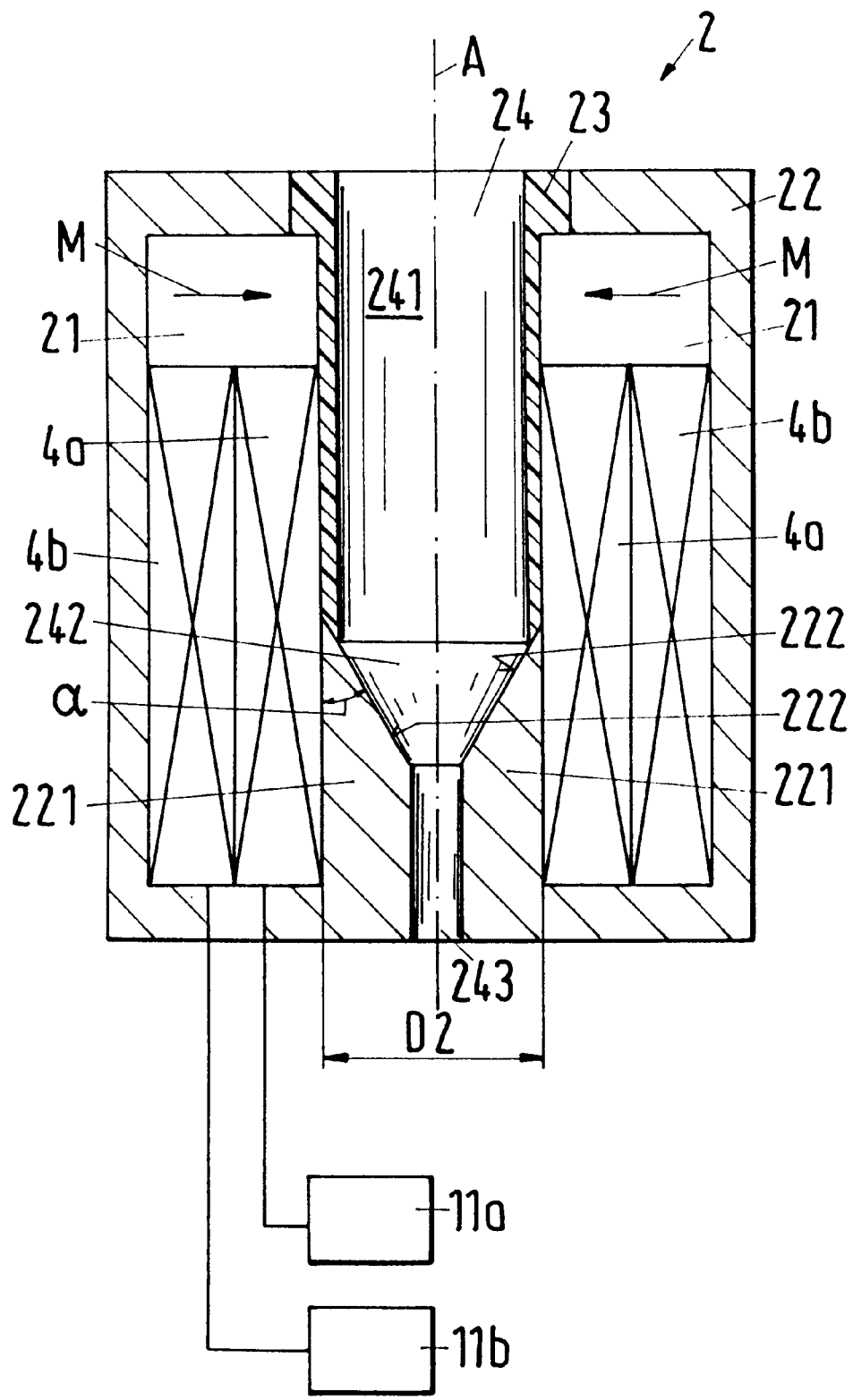
Figure 3:
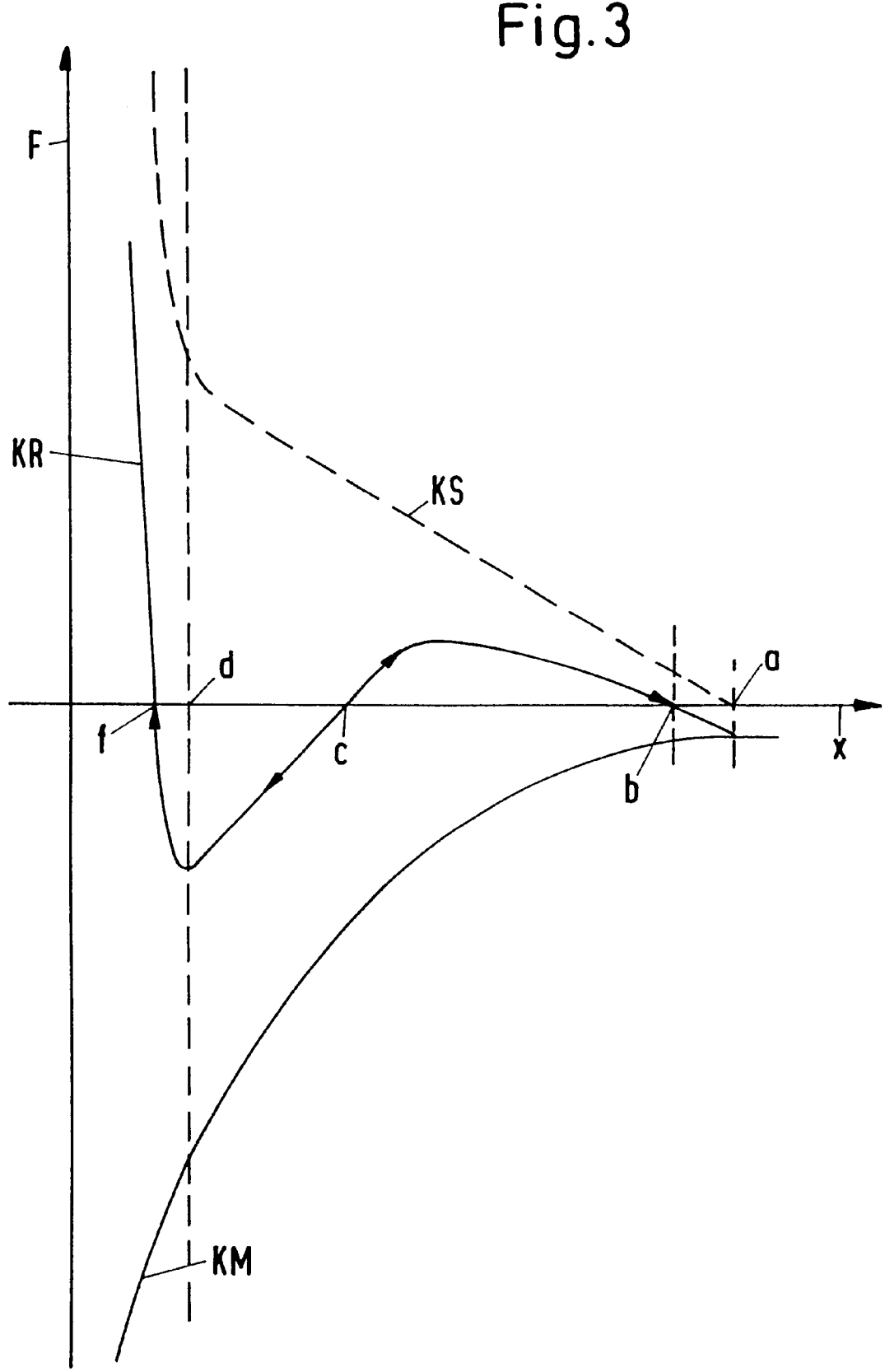
Figure 4:
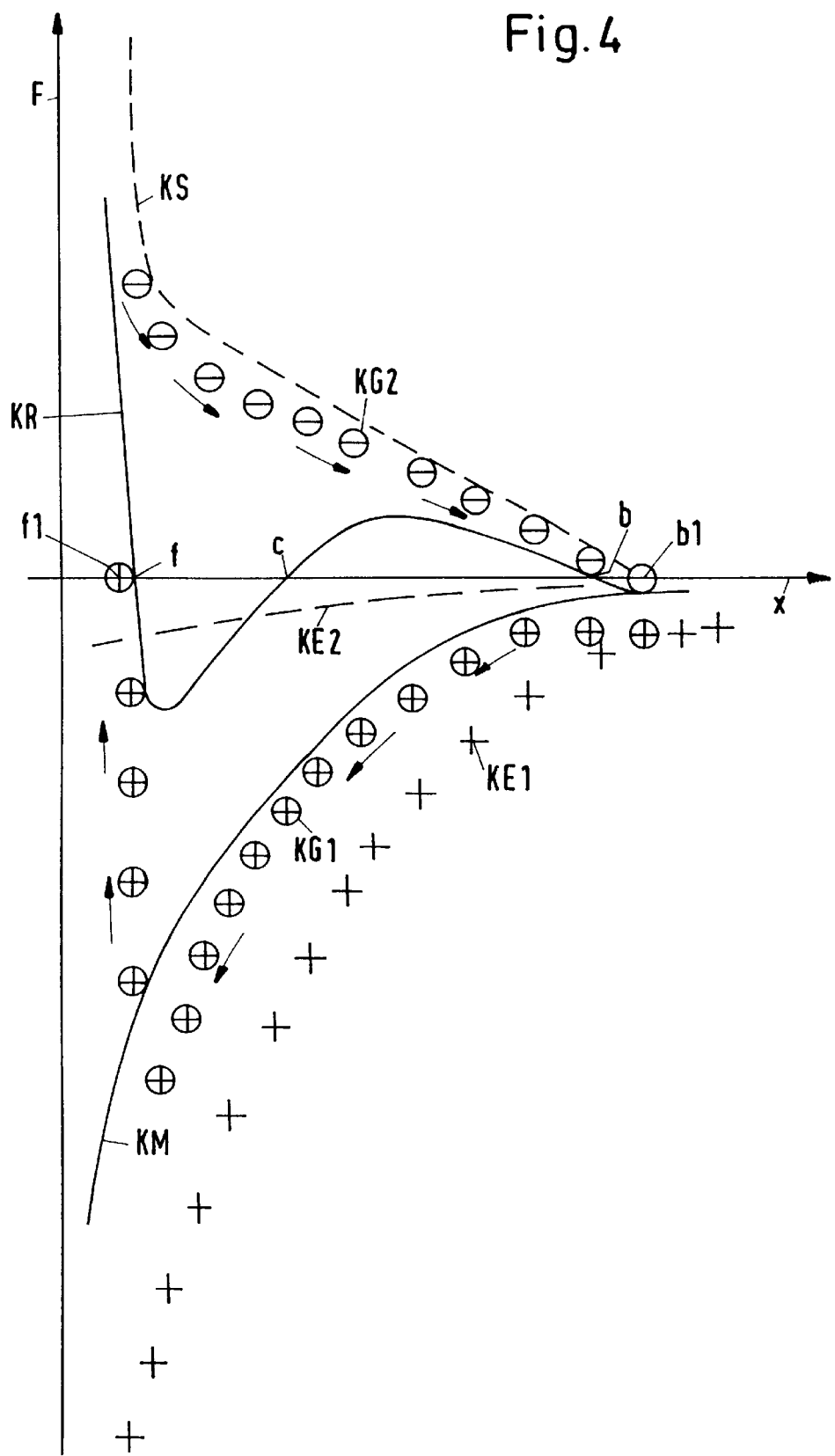
Figure 5:
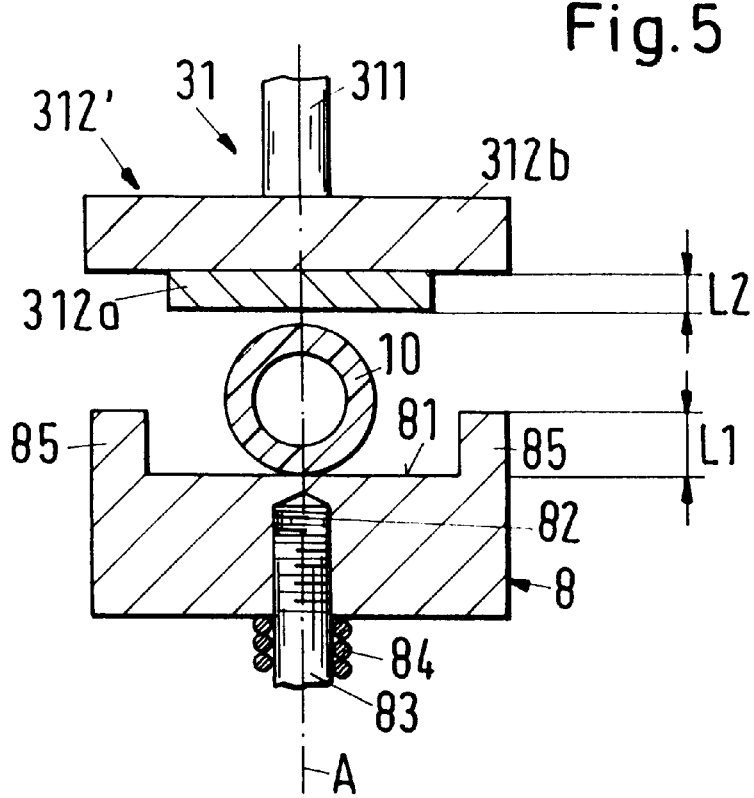
Figure 7:
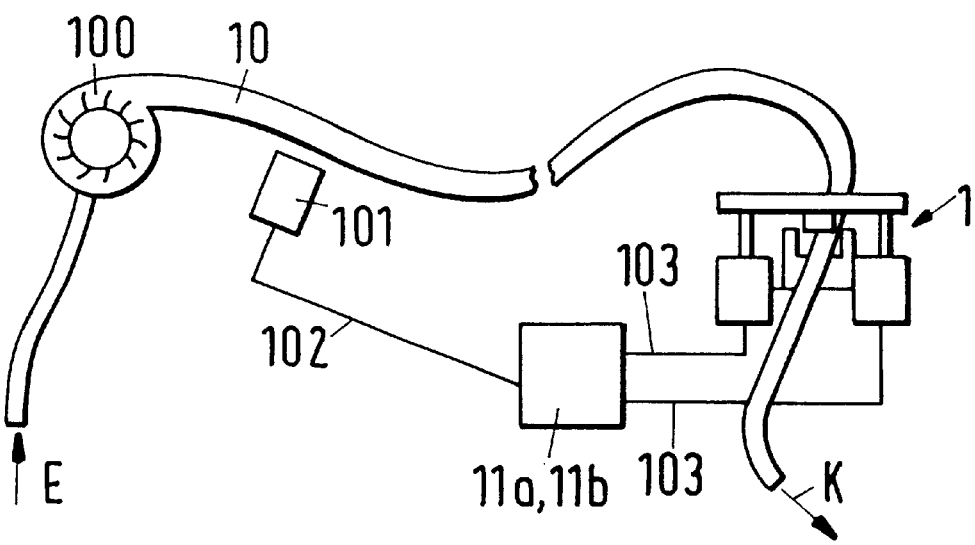
Figure 6:
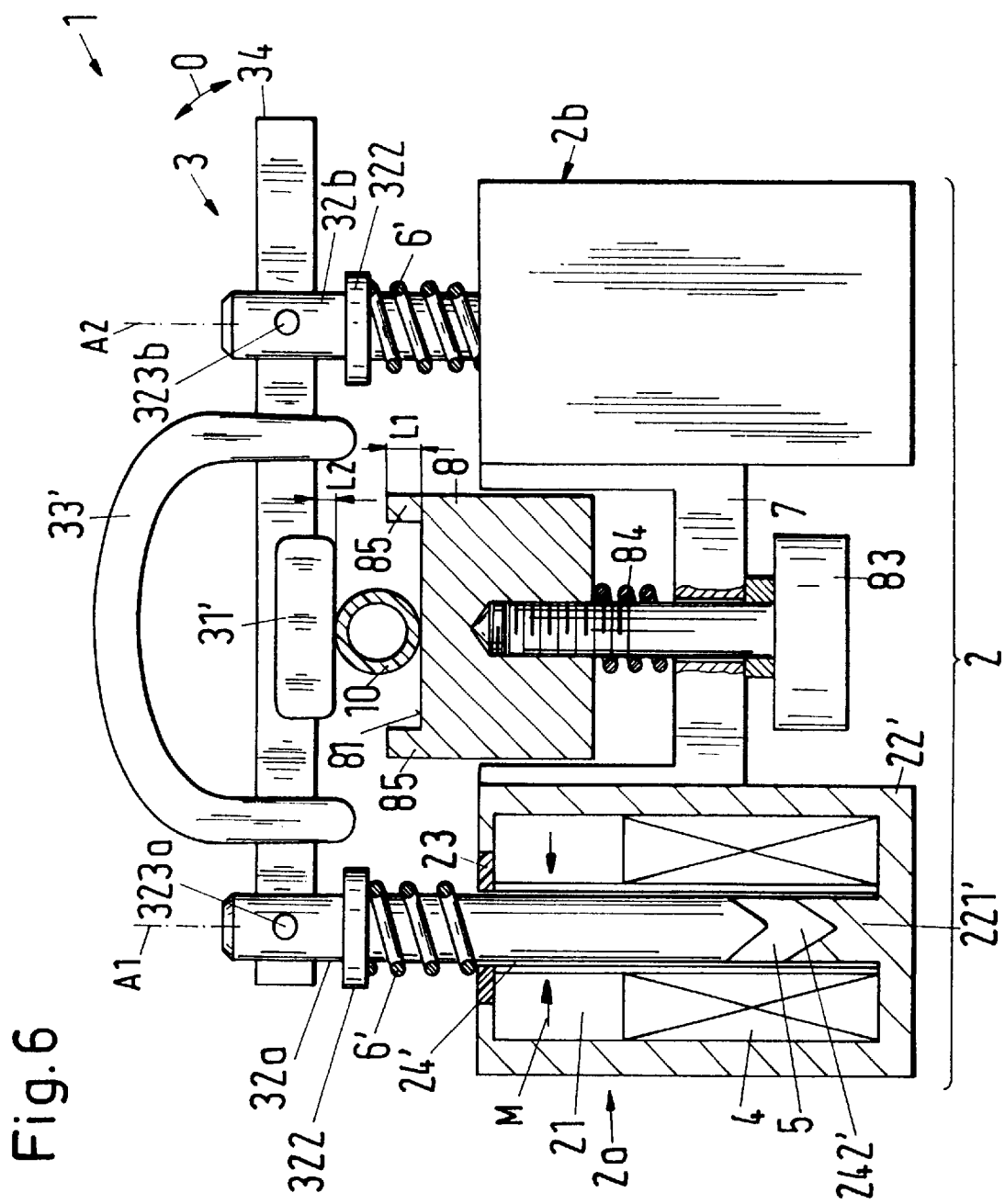

In the following the invention will be explained in more detail with reference to exemplary embodiments and with reference to the drawings. Shown in the partly schematic drawings are:

FIG. 1: a longitudinal section through a first exemplary embodiment of the clamping apparatus in accordance with the invention, FIG. 2: the permanent magnetic holding device of FIG. 1 (without a closing member), FIG. 3: a diagram with force-path characteristics, FIG. 4: as in FIG. 3, but however including characteristic curves for the switching into the closure position or into the open position respectively, FIG. 5: an embodiment of safety means for avoiding damage to the hose, FIG. 6: a second exemplary embodiment of the clamping apparatus in accordance with the invention, partly in section, and FIG. 7: a schematic illustration of a fluid system with a combination of a pump apparatus with a clamping apparatus in accordance with the invention.

In the following description the relative position designations such as "up", "down", "above", "below" etc. refer to the illustrations in the figures, but do not have a restrictive character, however.

FIG. 1 shows in a longitudinal section a first exemplary embodiment of a clamping apparatus in accordance with the invention which is provided in its entirety with the reference symbol 1. The clamping apparatus 1 comprises a closing member 3 with a closure piece 31 for clamping off a hose 10 and a permanent magnetic holding device 2 for holding the closing member 3 in two different stable equilibrium positions. For a better understanding FIG. 2 shows the permanent magnetic holding device 2 without the closing member 3 in an illustration analogous to FIG. 1.

The permanent magnetic holding device 2 (see FIG. 1 and FIG. 2) comprises a housing 22, the longitudinal axis of which is designated by A. The housing 22 is manufactured of a ferromagnetic material. The holding device 2 has a central passage 24 for the reception of the closing member 3. The passage 24 extends in the direction of the longitudinal axis A and has an upper cylindrical region 241 at which a conical region 242 adjoins, which then merges into a lower cylindrical region 243, the diameter of which is less than the diameter of the upper cylindrical region 241. The conical region 242 and the lower cylindrical region 243 are bounded by two extensions 221 of the housing 22 which extend upwardly in each case in the axial direction and of which the upper boundary surfaces 222 extend in each case at an inclination to the longitudinal axis A so that they form the conical region 242 of the passage 24. The half cone angle is designated by α. A sleeve 23, which is manufactured of a non ferromagnetic material, for example of a plastic, is inserted into the upper cylindrical region 241. In the housing 22 of the permanent magnetic holding device 2 between the sleeve 23 and the outer wall of the housing, two permanent magnets 21 are arranged, the magnetization of which, symbolically illustrated by the arrows M, is perpendicular to the longitudinal axis A. In the exemplary embodiment described here the north pole N lies in each case inwardly and the south pole S outwardly, which means that the magnetization M points in each case from the outside to the inside, that is, is directed towards the longitudinal axis A. For example the permanent magnets 21 are in each case designed in the shape of a rectangular parallelepiped and are arranged on both sides adjacently to the central passage 24; or the permanent magnets 21 are in each case designed as half shells which are arranged around the passage 24.

Beneath the permanent magnets 21 two coaxially arranged coils 4a, 4b are provided in the housing 22 and serve as actuation means in order to move the closing member 3 out of its open position into its closure position or vice versa respectively. Each of the coils 4a, 4b surrounds the passage 24, with the first coil 4a being arranged to lie inwardly with respect to the radial direction and the second coil 4b being arranged to lie outwardly around the first coil 4a. Each of the coils 4a, 4b can thus exert an electromagnetic force on the closing member 3 which is directed in the direction of the longitudinal axis A when it is fed with current. The control and supply devices 11a, 11b, which are known per se, for the coils 4a, 4b are symbolically illustrated in FIG. 2. Naturally embodiments with only one coil as actuation means for the closing member 3 are also possible. With two separate coils 4a, 4b however an advantageous fault tolerance can be realized, since in the case of a fault in one coil the closing member 3 can still be actuated by means of the other coil. Therefore separate control and supply devices 11a, 11b with separate amplifiers for the two coils 4a, 4b are also preferably provided.

The closing member 3 (see FIG. 1) comprises a bar 32 which is arranged in the sleeve 23 and of which the diameter D1 is matched to the inner diameter of the sleeve 23 in the upper cylindrical part 241 of the passage 24 so that the bar 32 is guided by the sleeve 23. The bar 32 is made of a ferromagnetic material and tapers conically at its lower end, with the half cone angle preferably being equal to the angle α at which the boundary surfaces 222 are inclined, so that an air gap 5 is present between the lower end of the bar 32 and the boundary surfaces 222 which is bounded with respect to the axial direction by two mutually parallel surfaces which extend at an inclination with respect to the longitudinal axis A. The closure piece 31 is secured at the lower end of the bar 32 and is formed here as a piston with a rod 311 and a head 312. The rod 311 extends through the lower conical region 243 of the passage 24 and ends at the head 312, which is arranged outside the housing 22 and serves to clamp off the hose 10. The closure piece 31 is manufactured of a non ferromagnetic material.

The upper end of the bar 32 protrudes out of the housing 22 and is provided with a grip 33, which serves as a mechanical actuation means for the closing member 3. The grip 33 is screwed on onto a thread 321 at the upper end of the bar 32. A spring element 6, which is executed as a spiral spring and which acts via the grip 33 on the closing member 3 and exerts a spring force on the latter that is directed upwards in the illustration, is arranged between the grip 33 and the housing 22 or the sleeve 23 respectively. The bias force of the spring element 6 and thus the spring force which is caused by it can be set by means of the grip 33. If the grip 33 is screwed further downwards on the thread 321, then the spring element 6 is compressed more strongly, through which the spring force which is exerted by it increases. If the grip 33 is screwed upwards on the thread 321, then the spring element relaxes, from which a reduction of the spring force which acts on the closing member 3 results.

Beneath the housing 22 a holder 7, which is secured at the housing 22, for a counter-piece 8 is provided for placing on the hose 10. The counter-piece 8 has a contact surface 81 for the hose 10 and is arranged in such a manner that the hose 10 can be clamped in between the closure piece 31 of the closing member 3 and the counter-piece 8. The counter-piece 8 is resiliently and displaceably journalled with respect to the axial direction in order to enable an adaptation to the diameter of the hose 10 and in order to damp the closure movement. For this the counter-piece 8 is provided with a threaded bore 82 into which an adjusting screw 83 engages, which extends through a threadless bore in the holder 7. A spring 84 is provided between the lower side of the counter-piece 8 and the holder 7, so that the counter-piece 8 is resiliently journalled with respect to the holder 7. Through rotation of the adjusting screw 83 the counter-piece 8 can be displaced upwards or downwards respectively in the direction of the longitudinal axis A, through which the clamping apparatus 1 can be adapted to the diameter of the respective hose 10 which is used.

The permanent magnetic holding device 2 can, as will be explained in more detail, hold the closing member 3 in two stable equilibrium positions, namely an open position which is illustrated in FIG. 1 in which the hose 10 is not or only slightly clamped so that the liquid can flow through the hose 10, and a closure position in which the hose 10 is clamped in between the closure piece 31 and the counter-piece 8 in such a manner that no more liquid can flow through the hose 10. In the open position (FIG. 1) the flow cross-section for the liquid in the hose 10 is a maximum. For closing, the closing member 3 is moved downwards in a manner which remains to be explained and thereby presses the hose 10 together in such a manner that the flow cross-section becomes zero. In this closure position of the closing member 3 the hose 10 is then clamped off.

For reasons of greater clarity the closure piece 31 is illustrated in FIG. 1 without contact with the hose 10. In practice however the hose 10 is usually also slightly clamped in between the closure piece 31 and the counter-piece 8 in the open position.

An essential feature of the invention is that the permanent magnetic holding device 2 can hold the closing member 3 in both equilibrium positions (open position and closure position). During the holding the clamping apparatus 1 requires no energy in the form of current, for which reason the clamping apparatus 1 is enormously thrifty with respect to the energy consumption.

In FIG. 1 the permanent magnetic flux which is generated by the permanent magnet 21 is symbolically illustrated by the two field lines PM, which are drawn in broken lines. The permanent magnetic flux PM flows from the north pole N of the permanent magnet through the sleeve 23 into the ferromagnetic bar 32, is conducted downwards in the axial direction by the latter, flows through the air gap 5 into the extension 221 of the housing 22 and is then conducted back to the south pole S of the permanent magnet 21 by the housing 22, first outwardly in the radial direction and then upwardly in the axial direction.

Likewise drawn in in FIG. 1 are two field lines EM (solid lines) of the electromagnetic flux which is generated by the coils 4a, 4b but is present only when the closing member is switched from the open position into the closure position or from the closure position into the open position. These switching processes will be explained further below.

In the following the holding of the closing member 3 in the two equilibrium positions will now be explained in more detail with reference to FIG. 3. Without restriction of the generality, forces which act downwardly, that is, in the direction towards the closure position, are illustrated and designated as negative, and forces which act upwardly as positive. During the holding in the open position or the closure position the coils 4a, 4b are deactivated, so that they exert no electromagnetic force on the closing member 3. Then substantially the following forces act on the closing member 3: The negative magnetic force which is exerted by the permanent magnet 21, a positive force which the hose 10 causes and which will be designated as the hose force in the following, as well as the positive spring force which the spring element 6 causes. The magnitude of these forces is dependent on a path coordinate x. The path coordinate x (see FIG. 1) specifies the distance between the contact surface 81 of the counter-piece 8 and the boundary surface of the head 312 of the closure piece 31 which faces it, with x=0 meaning that the head 312 of the closure piece 31 lies in contact on the contact surface 81 of the counter-piece 8.

Different force-path coordinates are plotted in FIG. 3 for the case that the coils 4a, 4b are deactivated, that is, are not fed with current. The path coordinate x increases to the right and the magnitude of the respective force F increases upwards for positive forces and downwards for negative forces.

The characteristic curve KS represents the hose force. For x=a (or x>a) the hose is completely open - the hose force is zero. As x becomes smaller the hose force at first increases approximately linearly in the range d<x<a. This range corresponds to the "collapsing" of the hose, which means that the hose is increasingly pressed together, through which the open flow cross-section in it is reduced. At x=d the hose is completely "collapsed", which means that it is clamped in in such a manner that the open flow cross-section in it is zero. On further reduction of x (f<x<d) the hose wall is compressed, which leads to a very steep rise in the hose force.

The magnetic characteristic curve KM reproduces the dependence of the permanent magnetic force on the closing member 3 in dependence on x. As x becomes smaller the air gap 5 between the bar 32 and the extensions 221 of the housing 22 become smaller, from which an increase of the permanent magnetic flux and thus of the magnetic force on the closing member 3 which is caused by it results. The gap 5 is preferably dimensioned such that it is just completely closed for x=0. Since the magnetic force is substantially proportional to the square of the magnetic flux, the magnitude of the magnetic force increases substantially quadratically with decreasing x. This dependence leads qualitatively to the characteristic curve KM which is illustrated in FIG. 3.

No special characteristic curve is drawn in in FIG. 3 for the positive spring force which the spring element 6 causes. The spring force depends substantially linearly on the path x, with the magnitude of the spring force becoming larger with decreasing x. Thus purely qualitatively the characteristic curve for the spring force behaves in the same manner as the characteristic curve KS of the hose force in its linear range (d<x<a). Since it is sufficient for the understanding, the characteristic curve KS will be considered representative for the sum of the hose force and the spring force which is caused by the spring element 6 in the following. For designs in which no spring element 6 is provided, the characteristic curve KS thus represents the dependence of the hose force on the path coordinate x and for preferred designs such as the one described here, in which the spring element 6 is present, the characteristic curve KS represents the dependence of the sum of the hose force and the spring force on the path coordinate x. Since the hose force has a path dependence in its linear range which corresponds to that of a spring, and the hose thus also acts approximately as a spring, the sum of the hose force and the force which is caused by the spring element 6 will be designated in the following as the spring force for the sake of simplicity. The latter contains both the force of the "hose spring" and that of the spring element 6.

The characteristic curve for the resultant total force which acts on the closing member 3 results from addition of the magnetic characteristic curve KM and the characteristic curve KS. The characteristic curve for the total force is designated in FIG. 3 by the reference symbol KR. As FIG. 3 shows, the characteristic curve KR has three zero crossings, namely at the values x=b, x=f and x=c. At these zero crossings the resultant total force on the closure piece 31 is zero, which means that for these three values, b, f and c, the closing member is in force equilibrium. Two of the equilibrium positions, namely x=f and x=b, are stable equilibrium positions. If for example the closing member 3 is in the position x=f and if it is deflected out of this position in the direction of decrease of the x coordinate, then the positive spring force predominates and causes an increase in x again, which means that the closing member 3 returns into the equilibrium position x=f. If the closing member 3 is deflected from the equilibrium position x=f in the direction of increase of the x coordinate, then the negative magnetic force predominates and pulls the closing member 3 back into the equilibrium position x=f. As a result, x=f is a stable equilibrium position. In an analogous manner it turns out that the value x=b also corresponds to a stable equilibrium position of the closing member 3. The stable equilibrium position x=f is the closure position of the closing member 3 and the stable equilibrium position x=b is its open position.

The third equilibrium position at x=c is a labile equilibrium position. If the closing member 3 is in the position x=c and if it is deflected only slightly out of this equilibrium position in the direction of increase of the x coordinate, then the spring force predominates, through which x is further increased until the closing member 3 assumes a stable equilibrium position (open position) at x=b. If the closing member 3 is deflected out of the position x=c in the direction of decrease of the x coordinate, then the negative magnetic force predominates, through which x is further decreased until the closing member assumes the other stable equilibrium position (closure position) at x=f.

Thus there exist exactly two stable equilibrium positions of the closing member 3, namely the open position and the closure position, in which the force which is exerted by the permanent magnet 21 on the closing member 3 and the spring force which acts on the closing member 3 permanently compensate one another. The permanent magnetic holding device 2 is a bistable, passive holding system, with passive being understood in the sense that no energy, e.g. in the form of current, need be supplied to the holding system in order to hold the closing member in the open position or in the closure position.

In order to match the two characteristic curves KM and KS to one another in such a manner that a desired resultant characteristic curve KS results, various measures are available, only several of which will be mentioned here in a non exhaustive listing.

The characteristic curve KS can be modified via the material properties of the material of which the hose 10 is manufactured and through the geometry of the hose 10, for example the thickness of the hose wall. Furthermore, the characteristic curve KS can be varied through the choice of the spring element 6 or via the bias force of the spring element 6, which can be set by means of the grip 33 (FIG. 1).

The modification or adaptation respectively of the characteristic curve KM for the magnetic force which is caused by the permanent magnets 21 can take place via: material, size, shape and strength of the permanent magnets 21, material properties such as the saturation magnetization, as well as the geometry of the components which conduct the permanent magnetic flux, that is, e.g. the bar 32, the extensions 221 and the housing 22. Thus the permanent magnetic force can for example be modified via the outer diameter D1 of the bar 32 (see FIG. 1) or via the extent D2 (see FIG. 2) of the extensions 221 in the radial direction.

In particular the path of the characteristic curve KM of the magnetic force can be modified via the angle $\alpha$ (FIG. 2), which determines the inclination of the boundary surfaces 222 of the extensions 221. For technical manufacturing reasons $\alpha$ is preferably chosen between 0° and 90°. Small values of $\alpha$ have as a result that the magnetic characteristic curve KM extends less steeply, that is, with a lower slope in particular for small values of x, whereas larger values of $\alpha$ make the magnetic characteristic curve KM steeper. For $\alpha=90°$ the boundary surfaces 222 extend perpendicular to the longitudinal axis A, which means that the conical region 242 of the passage 24 (FIG. 2) is not present.

Through these measures it is possible to match the two characteristic curves, namely the characteristic curve KM for the magnetic force and the characteristic curve KS for the sum of the spring force which is caused by the hose 10 and the spring element 6, to one another in such a manner that two stable equilibrium positions exist for the closing member 3 when no current is fed in into the coils 4a, 4b.

It will now be explained how the closing member 3 is brought from one stable equilibrium position into the other stable equilibrium position. It will first be assumed that the closing member is in its open position which is illustrated in FIG. 1 and is to be brought into the closure position. In the here described exemplary embodiment the two coils 4a, 4b (see FIG. 1, FIG. 2) are provided as actuation means for this. As already explained, the coils 4a, 4b are arranged in such a manner that they exert an electromagnetic force on the closing member 3 acting in the direction towards the closure position or in the direction towards the open position when they are activated through charging with current. The direction of the electromagnetic force depends in this on the polarity of the current which is fed into the coils 4a, 4b. Let it be agreed upon without restricting the generality that a current with a positive sign causes an electromagnetic force which is directed downwardly in the direction of the longitudinal axis A - that is, in the direction towards the closure position - and that a current with negative sign causes an upwardly directed electromagnetic force in the direction of the longitudinal axis A. In FIG. 1 the electromagnetic flux which results from a positive current is symbolically illustrated by the two field lines EM.

In an illustration which is analogous to FIG. 3, FIG. 4 shows a plurality of force-path characteristic curves. KS again designates the characteristic curve for the spring force which results from the hose 10 and the spring element 6; KM designates the characteristic curve of the magnetic force which is caused by the permanent magnet 21 and KR the characteristic curve of the resultant total force. The characteristic curves KM, KR relate to the case that the coils 4a, 4b are not charged with current. In this case the two stable equilibrium positions at x=b (open position) and x=f (closure position) exist for the closing member 3.

If now the coils 4a, 4b are charged with a positive current, then they cause an electromagnetic flux which exerts a negative electromagnetic force on the closing member 3. For a positive current the electromagnetic flux and the permanent magnetic flux have the same direction, which means that they add in their effect. The total magnetic force, that is, the sum of the permanent magnetic force and the electromagnetic force, is proportional to the square of the sum of the electromagnetic and the permanent magnetic flux. This total magnetic force or its dependence on x respectively is illustrated in FIG. 4 by the characteristic curve KE1 which is drawn in with the + symbols. In this the + symbol is meant to indicate that the current for the coils 4a, 4b has a positive sign. The characteristic curve KG1, which represents the total force which acts on the closing member 3 in the case of positive current through the coils 4a, 4b, results from the addition of the characteristic curves KS and KE1. This characteristic curve, which is designated by KG1, is illustrated with the ⊕ symbols. As FIG. 4 shows, the characteristic curve KG1 now has only one zero crossing, at x=f1, with f1<f. This zero crossing at f1 is a stable equilibrium position. For all values of x which are greater than f1 the total magnetic force (characteristic curve KE1) is always greater in magnitude than the spring force (characteristic curve KS) so that the resultant total force (characteristic curve KG1) is always negative. If thus the closing member is initially in its open position (x=b) and if then a positive current is fed in into the coils 4a, 4b, then the closing member moves into the equilibrium position f1. After switching off of the current through the coils 4a, 4b, the closing member 3 assumes the stable equilibrium position x=f on the characteristic curve KR and is thus in its closure position. The hose 10 is clamped off, which means that it is clamped in between the closure piece 31 and the counterpiece 8 in such a manner that no more liquid can flow through it.

In order to move the closing member 3 out of the open position into the closure position, it is not necessary to leave the positive current switched on until the closing member 3 has assumed the equilibrium position at x=f1. The current through the coils 4a, 4b can already be switched off as soon as the closing member 3 is at a path coordinate x which is less than c. On the characteristic curve KR, which represents the current-less case, one is then namely already to the left of the labile equilibrium position x=c, so that the closing member 3 assumes its stable equilibrium position at x=f (closure position) automatically, which means without the assistance of the electromagnetic force or the electromagnetic flux respectively.

In order to move the closing member 3 out of the closure position into the open position, the coils 4a, 4b are charged with a negative current. In this case the electromagnetic flux which is generated by the activated coils 4a, 4b is directed opposite to the electromagnetic flux, which means that these two fluxes weaken one another in their effect. The total magnetic force which is exerted by the permanent magnets 21 and the activated coils 4a, 4b on the closing member 3 is thus proportional to the square of the difference of the magnitude of the permanent magnetic flux and the magnitude of the electromagnetic flux for a negative current. The path dependence of this total magnetic force for the case of a negative current in the coils 4a, 4b is reproduced by the characteristic curve KE2 in FIG. 4, which is illustrated with the ⊖ symbols. In this the - symbol is meant to indicate that the current for the coils 4a, 4b has a negative sign. The characteristic curve KG2, which represents the total force which acts on the closing member 3 in the case of negative current through the coils 4a, 4b, results from addition of the characteristic curves KS and KE2. This characteristic curve, which is designated by KG2, is illustrated with the ⊖ symbols. As FIG. 4 shows, the characteristic curve KG2 now has only one zero crossing, at x=b 1, with b1>b. This zero crossing at b1 is a stable equilibrium position. For all values of x which are smaller than b1, the total magnetic force (characteristic curve KE2) is always smaller in magnitude than the spring force (characteristic curve KS), so that the resultant total force (characteristic curve KG2) is always positive. If thus the closing member 3 is initially (that is, prior to activation of the coils 4a, 4b) in its closure position (x=f and if a negative current is then fed in into the coils 4a, 4b, then the closing member 3 moves into the equilibrium position b1. After the current through the coils 4a, 4b is switched off, the closing member 3 assumes the stable equilibrium position x=b on the characteristic curve KR and is thus in its open position.

Analogously as was described above, it is also sufficient for the process of opening when the negative current in the coils 4a, 4b remains switched on until the closing member 3 is in a position with x>c. If then the current is switched off, the closing member 3 continues to move until it has assumed its stable equilibrium position at x=b, because it is already to the right of the labial equilibrium position x=c for the current-less case.

The positive or negative current can be set in a simple way by means of the control and supply devices 11a, 11b for the coils 4a, 4b in such a manner that at least qualitatively the characteristic curves KE1 and KE2 which are shown in FIG. 4 result. The characteristic curve KE2 which is decisive for the opening is preferably set in such a manner that it extends as close beneath the x axis as possible. In practice it is normally not possible to set the characteristic curve KE2 in such a manner that it lies exactly on the x axis.

As described above the closing member can thus be moved out of the open position into the closure position or out of the closure position into the open position through charging the coils 4a, 4b with a positive or with a negative current. For this the direction (the sign) and the magnitude of the current are in each case set in such a manner that only one stable equilibrium position (open or closed) now exists for the closing member 3 as long as the current flows in the coils 4a, 4b.

As already mentioned, it is by no means necessary to provide two separate coils 4a, 4b. The exemplary embodiment described here functions in exactly the same way even when only one coil is provided. The design with two coils however has the advantage of being fault tolerant. In normal operation the switching between the open position and the closure position of the closing member 3 is caused by charging both coils 4a, 4b with current. If now one coil 4a or 4b (or one of the supply and control devices 11a, 11b)

fails, e.g. as a result of the breaking of an electrical line, then the clamping apparatus 1 remains completely capable of functioning because the switching into the open position or the closure position respectively can still be caused with the other coil 4b or 4a. If only one of the two coils 4a or 4b is used for the switching, a correspondingly larger current must naturally flow in this coil in order to generate substantially an electromagnetic flux which is equally large as in the case that both coils are used for generating the electromagnetic flux.

The clamping apparatus 1 can furthermore be mechanically actuated in a simple way, for example when both coils 4a, 4b or the entire power supply fail, The grip 33 (see FIG. 1) is provided for this. If the closing member 3 is in the open position, then it can be brought into the closure position through the exertion of a downwardly directed (negative) force, for example through a pressure or a blow by hand. This force need merely be sufficient for moving the closing member 3 into a position with x<c (see FIG. 3). Then the permanent magnetic holding device 2 automatically ensures that the closing member 3 assumes and maintains its closure position at x=f. On the contrary the closing member 3 can be brought from the closure position into the open position in an analogous way through the exertion of an upwardly directed (positive) force on the grip 33, for example through drawing by hand.

If the clamping apparatus is electromagnetically actuated, a switching time of less than 100 milliseconds, for example about 80 milliseconds, can be realized without problem. By the switching time is meant the time which the closing member 3 requires in order to move from the one equilibrium position into the other equilibrium position.

A further advantageous measure consists in providing safety means which are designed such that the distance between the counter-piece 8 and the closure piece 31 of the closing member 3 which cooperates with it is always greater than a minimum value. Through this measure it can be prevented, in particular in the closing process, in which the closure piece 31 moves downwards and presses the hose 10 against the counter-piece 8, that the hose 10 is damaged or severed. In addition a damping takes place through the spring 84.

FIG. 5 illustrates a possible embodiment of such safety means. The counter-piece 8 has two projections 85 which protrude in the axial direction in each case by an amount 11 beyond the contact surface 81 for the hose 10. The head 312' of the closure piece 31 of the closing member 3 comprises two disc-like elements 312a and 312b, which are arranged one above the other relative to the longitudinal axis A. The lower element 312a, which is nearer to the counter-piece 8, has an axial height 12, by which its extension in the direction of the longitudinal axis A is meant, which is less than the amount 11 by which the projections 85 protrude beyond the contact surface 81 of the counter-piece 8. In the radial direction the lower element 312a is dimensioned such that it fits between the two projections 85. The upper element 312b, which is further distant from the counter-piece 8, is on the contrary dimensioned in the radial direction such that it does not fit between the projections 85.

If the closing member 3 and thus the closure piece 31 is now moved downwards, then it moves at most to such an extent that the upper element 312b lies in contact on the two projections 85. This is the minimum possible distance between the closure piece 31 and the contact surface 81 of the counter-piece 8. This minimum amounts to 11–12. Thus a gap between the lower element 312a of the closure piece 31 and the contact surface 81 which has at least the axial height 11–12 is always available for the hose 10. It is self evident that 11 and 12 are dimensioned or are matched to the respective hose which is used such that on the one hand 11–12 is not greater than d (see FIG. 3), that is, the value of x at which the flow cross-section in the hose 10 is completely closed, and on the other hand a severing of the hose 10 during the closing of the clamping apparatus 1 is reliably prevented. In practice it has in particular proven useful when the difference 11–12 amounts to approximately 1.2 to 1.8 times the wall thickness of the hose 10.

As an additional safety measure the counter-piece 8 is resiliently journalled with respect to the axial direction by means of the spring 84 as explained above, so that the closing or the clamping off of the hose 10 respectively takes place in a damped manner.

FIG. 6 shows, partly in section, a second exemplary embodiment of the clamping apparatus 1 in accordance with the invention which has proved useful in practice. The theoretical method of construction is identical to that of the first exemplary embodiment and will thus not be explained further. Parts which have identical functions or which are equivalent are always provided with the same, already explained reference symbols as in the first exemplary embodiment, with a prime ' partly being applied to the reference symbol in addition in order to indicate the different design. In the following the differences from the first exemplary embodiment will be described; otherwise the explanations with respect to the first exemplary embodiment also hold in an analogous manner for the second exemplary embodiment.

In the second exemplary embodiment in accordance with FIG. 6 the closing member 3, which is illustrated in its open position in FIG. 6, comprises two bar-like limbs 32a, 32b and a transverse bar 34 at which the limbs 32a, 32b are fastened with a spacing and parallel to one another. The two limbs 32a, 32b extend in each case substantially perpendicularly to the transverse bar 34. The closure piece 31' is arranged at the transverse bar 34 between the two limbs 32a, 32b, but can also be realized through the transverse bar 34 itself. The permanent magnetic holding device 2 comprises two permanent magnetic holders 2a, 2b, one of which is illustrated in section. Both holders 2a, 2b are designed alike and in each case receive one of the two limbs 32a, 32b, which means that the limb 32a is held by the holder 2a and the limb 32b by the holder 2b.

With respect to the holding of the closing member 3 in the two stable equilibrium positions (open position and closure position) the two limbs 32a, 32b and the permanent magnetic holders 2a, 2b which in each case surround them have functions which are analogous to those of the bar 32 and the permanent magnetic holding device 2 of the first exemplary embodiment. Since however in the second exemplary embodiment the closure piece 31' is arranged at the transverse bar 34, instead of the passage 24 of FIG. 1 a cut-out 24' is provided at each permanent magnetic holder 2a, 2b which extends in each case in the direction of the longitudinal axis A1 and A2 respectively of the permanent magnetic holder 2a and 2b respectively and ends with a conical region 242' in the interior of the housing 22'. This end is formed by the extension 221' of the housing 22', which corresponds to the two extensions 221 in FIG. 2. The end of the limb 32a and 32b respectively which is arranged in the cut-out 24' is in each case designed conically, in a manner analogous to that of the bar 32 of the first exemplary embodiment.

In FIG. 6 only one coil 4 for producing the electromagnetic force for the change between the two stable equilibrium positions is illustrated in the permanent magnetic holder 2*a*. Naturally in each case two separate coils with separate control and supply devices 11*a*, 11*b* can also be provided in each holder 2*a*, 2*b* in the second exemplary embodiment as well in a manner analogous to that described above in order to realize an advantageous fault tolerance.

For each limb 32*a*, 32*b* a spring element 6' is provided in order to exert a spring force on the closing member 3 which is directed upwardly, that is, in the direction of the open position. At the part of each limb 32*a*, 32*b* which protrudes out of the housing 22' a plate 322 is in each case provided on which the spring element 6' is supported. With its other end the spring element 6' lies in contact on the housing 22' or on the sleeve 23 respectively which is fitted in into the cut-out 24'. The function of the spring elements 6' corresponds to that of the spring element 6 in FIG. 1. The spring elements 6' cause a spring force on the closing member 3 which counteracts the force which is caused by the permanent magnets 21.

The holder 7 for the counter-piece 8 is arranged between the two permanent magnetic holders 2*a*, 2*b* so that the counter-piece 8 lies with its contact surface 81 opposite to the closure piece 31'. In the same way as in the first exemplary embodiment the counter-piece 8 can be displaced by means of the adjusting screw 83 with respect to the direction of the parallel longitudinal axes A1, A2 and is resiliently journalled in the holder 7 by means of the spring 84. In order to simplify the laying in of the hose 10 into the clamping apparatus 1 the limbs 32*a*, 32*b* are in each case connected to the transverse bar 34 by means of pins 323*a*, 323*b*. After removal of the pin 323*b* the transverse bar 34 can be pivoted upwardly about the pin 323*a*, as indicated by the arrow 0, so that the hose 10 can be laid onto the contact surface 81 of the counter-piece 8. Then the transverse bar 34 is pivoted downwards and the pin 323*b* is inserted.

The grip 33' is attached to the transverse bar as a mechanical actuation means. Through exertion of a downwardly directed force on the grip 33', for example through pressing by hand, the closing member can be brought from the open position into the closure position. Conversely, through exertion of an upwardly directed force on the grip 33', for example through drawing by hand, the closing member 3 can be brought from the closure position into the open position.

As a safety means for avoiding a damage to or a severing of the hose 10 the two projections 85 which protrude beyond the contact surface 81 for the hose 10 in the axial direction in each case by an amount 11 are also provided at the counter-piece 8 in the second exemplary embodiment. The closure piece 31' protrudes downwardly with respect to the axial direction beyond the transverse bar by an amount 12<11 and is dimensioned in the direction perpendicular thereto such that it fits between the two projections 85. The minimal possible distance 11–12 between the closure piece 31' and the contact surface 81 of the counter-piece 8 results when the transverse bar 34 lies in contact on the two projections 85.

In order to move the closing member 3 out of the open position into the closure position or out of the closure position into the open position, the coils 4 are charged with a positive or a negative current in a manner analogous to that described above for the first exemplary embodiment. In the two equilibrium positions (open position, closure position) the closing member 3 is passively magnetically held - without current being supplied - by the two permanent magnetic holders 2*a*, 2*b* against the spring force of the springs 6' and of the "hose spring".

FIG. 7 shows in a schematic illustration an exemplary embodiment of a fluid system for biological fluids which comprises the combination of a pump apparatus 100 for forwarding a biological fluid with a clamping apparatus 1 in accordance with the invention. The fluid system is for example a heart-lung machine for maintaining the blood circulation in the body of a patient. The pump apparatus 100 is a blood pump, the input of which is connected to the blood circulation of the patient, so that the blood can flow out of the body to the blood pump 100, as the arrow E indicates. The blood pump 100 forwards the blood in a hose 10 which is connected to its output. Furthermore, a clamping apparatus 1 in accordance with the invention is provided, which can be designed in accordance with the first or the second exemplary embodiment. The hose 10 is passed through the clamping apparatus 1 and lies in contact on the contact surface 81 of the counter-piece 8. Downstream from the clamping apparatus 1 the hose 10 is connected to the blood circulation of the patient so that the forwarded blood is supplied to the body circulation, as the arrow K indicates.

Downstream from the output of the blood pump 100 and upstream from the clamping apparatus 1 a bubble detector 101 is provided, which monitors whether air bubbles are present in the blood which flows through the hose 10. The bubble detector is connected via a signal line 102 to the control and supply device(s) 11*a*, 11*b* of the clamping apparatus 1. The control and supply devices 11*a*, 11*b* are connected via lines 103 to the coils of the clamping apparatus 1.

During normal operation the closing member 3 of the clamping apparatus 1 is in its open position so that the forwarded blood can flow into the body of the patient. If the bubble detector detects an air bubble in the hose 10, then it transmits a signal to the control and supply devices 11*a*, 11*b*, which then feed in a corresponding current into the coils of the clamping apparatus 1 so that the closing member 3 is moved into the closure position and clamps off the hose 10 between the closure piece 31, 31' and the contact surface 81. Then the flow connection is interrupted and no more blood can flow through the clamping apparatus 1. Since switching times of less than 100 milliseconds and in particular of at most 80 milliseconds can be realized without problem with the clamping apparatus 1 in accordance with the invention, the clamping apparatus 1 can close the flow connection for the blood before the bubble which was detected by the bubble detector 101 has passed the clamping apparatus 1. It is thus reliably avoided that the air bubble enters into the body of the patient. After removal of the air bubble, for example through ventilation of the hose 10, the control and supply devices 11*a*, 11*b* can switch the closing member into the open position again through corresponding current charging of the coils of the clamping apparatus 1.

Since the clamping apparatus 1 in accordance with the invention requires current only for the switching over between the open position and the closure position, but not for holding the closing member 3 in the stable equilibrium positions (open position and closure position) however, the clamping apparatus 1 has a very low energy or current consumption respectively and is thus also suitable in particular for portable systems.

In addition the clamping apparatus 1 can be manually actuated very rapidly and in a simple way. Through pressing onto the grip 33; 33' or drawing at the grip 33; 33' respectively the closing member 3 can be moved from the open position into the closure position or vice versa respectively. Thus the clamping apparatus 1 can be actuated very rapidly and reliably even in the event of a failure of the power supply or in the event in a fault in the coils.

It is self evident that in addition to the bubble detector 101 other monitoring means can also be present in the fluid system and can cause a switching over of the clamping apparatus 1 out of the open position into the closure position and vice versa by means of a control signal.

Naturally the clamping apparatus 1 in accordance with the invention is also suitable for fluid systems in which preferably biological liquids or fluids other than blood are transported, e.g. infusion solutions or nutrient solutions in bio-reactors.

What is claimed is:

1. Clamping apparatus in combination with a hose, for clamping off the hose in a fluid system for biological fluids, comprising, a movably arranged closing member having a closing piece clamping off the hose, further comprising a permanent magnetic holding device which is arranged and designed in such a manner that it can hold the closing member against a force in two different stable equilibrium positions, namely an open position and a closed position, without it being necessary to supply energy to the permanent magnetic holding device for the holding in the respective equilibrium position, and comprising actuation means in order to move the closing member out of the open position into the closed position.

2. Clamping apparatus in accordance with claim 1, in which the actuation means comprise at least one coil which is arranged in such a manner that it can exert an electromagnetic force on the closing member which acts in the direction towards the closing position or in the direction towards the open position.

3. Clamping apparatus in accordance with claim 1, in which the closing member comprises two limbs and a transverse bar, with the limbs being connected at a spacing from one another to the transverse bar, in which the permanent magnetic holding device comprises two permanent magnetic holders, each of which surrounds a respective limb, and in which the closing piece is arranged at the transverse bar between the two limbs.

4. Clamping apparatus in accordance with claim 3, in which for each limb of the closing member at least one coil which surrounds the limb is provided for exerting an electromagnetic force on the limb.

5. Clamping apparatus in accordance with claim 1, in which two separate coils are provided as actuation means for the closing member or for each limb of the closing member, with in each case a separate control and supply device being provided for each of the separate coils.

6. Clamping apparatus in accordance with claim 1, in which the actuation means comprise mechanical actuation means.

7. Clamping apparatus in accordance with claim 1, comprising at least one spring element which acts on the closing member and which is arranged in such a manner that the spring force acts counter to the magnetic force which the permanent magnetic holding device exerts on the closing member.

8. Clamping apparatus in accordance with claim 1, comprising a counter-piece for placing the hose on, which is arranged in such a manner that the hose can be clamped in between the closing piece of the closing member and the counter-piece.

9. Clamping apparatus in accordance with claim 8, in which the counter-piece is resiliently and displaceably journalled.

10. Clamping apparatus in accordance with claim 8, comprising safety means which are designed such that the distance between the counter-piece and the closing piece of the closing member which cooperates with it is always greater than a minimum value.

11. Combination of a pump apparatus for forwarding a biological fluid, with a clamping apparatus in accordance with claim 1.

* * * * *